United States Patent [19]

Wardlaw

[11] 4,156,570

[45] May 29, 1979

[54] APPARATUS AND METHOD FOR MEASURING WHITE BLOOD CELL AND PLATELET CONCENTRATIONS IN BLOOD

[75] Inventor: Stephen C. Wardlaw, Branford, Conn.

[73] Assignees: Robert A. Levine; James V. Massey, III, both of Trumbull, Conn.; part interest to each

[21] Appl. No.: 788,509

[22] Filed: Apr. 18, 1977

[51] Int. Cl.[2] .......................... G01N 33/16; G01N 1/00; G01N 9/30

[52] U.S. Cl. .......................... 356/36; 73/432 A; 73/747; 356/39; 356/427

[58] Field of Search .......................... 356/36, 39, 167, 197; 73/149, 64.4, 323; 128/2 G; 210/DIG. 23; 364/555

[56] References Cited

U.S. PATENT DOCUMENTS

| | | | |
|---|---|---|---|
| 2,973,580 | 3/1961 | Brown | 33/143 B |
| 3,561,877 | 2/1971 | Makada et al. | 73/149 |
| 3,582,218 | 6/1971 | Anderson | 356/197 |
| 3,916,205 | 10/1975 | Kleinerman | 356/36 |
| 4,027,660 | 6/1977 | Wardlow et al. | 73/149 |
| 4,031,399 | 6/1977 | Klein et al. | 250/461 B |
| 4,054,387 | 10/1977 | Wittome | 356/170 |

OTHER PUBLICATIONS

Circon, "Metrology System", Advertisement on MV9600, MIcrovideo from Circon Corp., Santa Barbara Airport, Goleta, Cal. 93017.

Seiverd; C. E. "Hematology For Medical Technologists", Lea & Febiger 1972, pp. 329–330.

*Primary Examiner*—John K. Corbin
*Assistant Examiner*—Wm. H. Punter
*Attorney, Agent, or Firm*—William W. Jones

[57] ABSTRACT

An apparatus and method for measuring the linear extent and hence the concentration of several constituent blood cell types which are contained in the buffy coat of a centrifuged sample of anticoagulated blood.

14 Claims, 4 Drawing Figures

APPARATUS AND METHOD FOR MEASURING WHITE BLOOD CELL AND PLATELET CONCENTRATIONS IN BLOOD

This invention relates to a method and apparatus for determining the approximate granulocyte and mononuclear white cell count, as well as platelet counts in a sample of centrifuged anticoagulated blood. More particularly, this invention relates to a method and apparatus for measuring the linear extent of the buffy coat constituents of a centrifuged sample of anticoagulated blood, which buffy coat has been elongated in accordance with the method and apparatus disclosed in U.S. Patent Application Ser. No. 673,058, filed Apr. 2, 1976, now U.S. Pat. No. 4,027,660.

A new technique has been devised for measuring the approximate granulocyte and mononuclear white cell counts, as well as platelet counts in a centrifuged sample of anticoagulated blood. This technique involves the introduction of the blood sample into a tube, preferably a capillary tube, which contains an elongated body which, when the blood sample is centrifuged and thus separated into its constituent cell layers, floats upon the red cell layer and combines with the tube bore to form a free volume inside of the tube which free volume is of restricted size. The buffy coat of the blood sample, which contains all of the cell types to be measured, settles into this resticted free volume and its axial extent is thus elongated over what it is ordinarily. Thus the axial distance between the interfaces of the respective buffy coat cell layers is increased accordingly. Measurement of the increased distance between the upper and lower interfaces or boundries of each cell layer provides an indication of the volume of the cell layer, and thus the number of cells in the cell layer, so long as the free space constitutes a known geometrical shape and the cells are of normal size or normally distributed.

To enhance the apparent separation of the constituent cell layers and to aid in more sharply defining the interfaces between adjacent cell layers, a fluorescent stain is added to the blood sample, the stain being one that is absorbed to differing degrees by the various cell layers so that the different cell layers can be distinguished from each other by their differential coloration. Acridine orange is one such stain which has been found to be useful for this purpose.

This invention relates to an apparatus and method for making sufficiently accurate linear measurements of the distance between the upper and lower interfaces in each component cell layer in the centrifuged axially elongated buffy coat which has been enhanced in accordance with the above-noted new technology.

It has been noted that when a blood sample is prepared for measurement in accordance with the technology outlined above, the interface of meniscus between adjacent cell type layers may provide a wavy, uneven dividing line between the cell layers when viewed in a circumferential direction about the tube which contains the blood sample. This uneven meniscus can lead to errors in layer volume determination depending on whether one happens to measure from the high or low side of the meniscus. This error can be magnified if the other meniscus of the layer being measured also forms in an uneven or wavy manner. In order to minimize the degree of error in measurement which this phenomenon can induce, I prefer to rotate the tube about its axis while the axial (longitudinal) measurements are being made. In this way the meanderings of the meniscus edge which are seen through the tube are visually averaged so that even the most uneven and wavy meniscus encountered in this technology will appear to be a straight line perpendicular to the longitudinal axis of the tube. This visual averaging minimizes the degree of error which could be made while measuring a wave meniscus. Furthermore, it does not alter the appearance of a properly formed meniscus. The tube should be rotated at a high enough rate so that the waviness in the meniscus blends into a straight line, but not so high a rate that the cell layers in the tube will be disturbed or altered. The precise minimal rate of rotation needed varies with the degree of illumination, the brighter the illumination, the higher minimum rate of rotation that will be needed to "average out" the meniscus, however, whether a sufficient rotational rate is being imparted to the tube is readily observable by one making the measurement. In general, a rotational velocity range of 600 r.p.m. to 1200 r.p.m. will prove satisfactory for performance of the measurement.

The apparatus or instrument of this invention includes a support for holding the tube containing the centrifuged blood sample to be measured. The support engages the tube at each of its ends so as to leave the cell layers unobstructed and the support has basically two parts. One part is preferably a passive part which engages one end of the tube and may be itself rotatable or non-rotatable, so long as it does not impede rotation of the tube. The other part of the support is, in effect, a chuck which grips the other end of the tube tightly enough to impart the desired rotation to the tube when the chuck is rotated. The chuck is preferably made of an elastomeric material, takes the form of an annulus which encircles the outside surface of the end of the tube, and is driven by a small electric motor.

The support and motor are mounted on a stage which is, in turn, movably disposed in a housing which forms a casing for the instrument. Movement of the stage within the casing is of a linear reciprocal nature and the stage may be mounted in the casing in any conventional manner which will enable the linear reciprocal movement of the stage to occur with respect to the casing. Preferably, a screw-type actuator is connected to the stage and is operable, upon rotation, to move the stage linearly with respect to the casing. A preferably parallax-free optical system with a reference line therein is included to line-up with each meniscus during measurement. Electrical means are operably connected tp the actuator screw for measuring the extent of rotation of the screw, which is, in turn, proportional to the extent of linear movement of the stage. Further electrical means are included in the preferred embodiment of the instrument to provide a system for storing and reading the various constituent layer thicknesses measured.

It is, therefore, an object of this invention to provide an apparatus and method for measuring the distance between the upper and lower menisci in a cell component layer of a centrifuged anticoagulated blood sample.

It is a further object of this invention to provide an apparatus and method of the character described wherein provision is made for producing an evenly appearing meniscus where the actual meniscus may be, in fact, uneven, tilted, or even.

It is yet another object of this invention to provide an instrument which automatically converts the distances between the several white blood cell layer interfaces to digital representations of the approximate concentrations of the respective white blood cell constituents when the different cell types are of different size and possess different packing characteristics.

It is yet another object of this invention to provide an apparatus of the character described which provides for electrically produced visual numerical indications of the several cell type layers in the buffy layer of a centrifuged blood sample.

These and other objects and advantages of the invention will become more readily apparent from the following detailed description of a preferred embodiment of the invention taken in conjunction with the accompanying drawings, in which.

Figure 1:
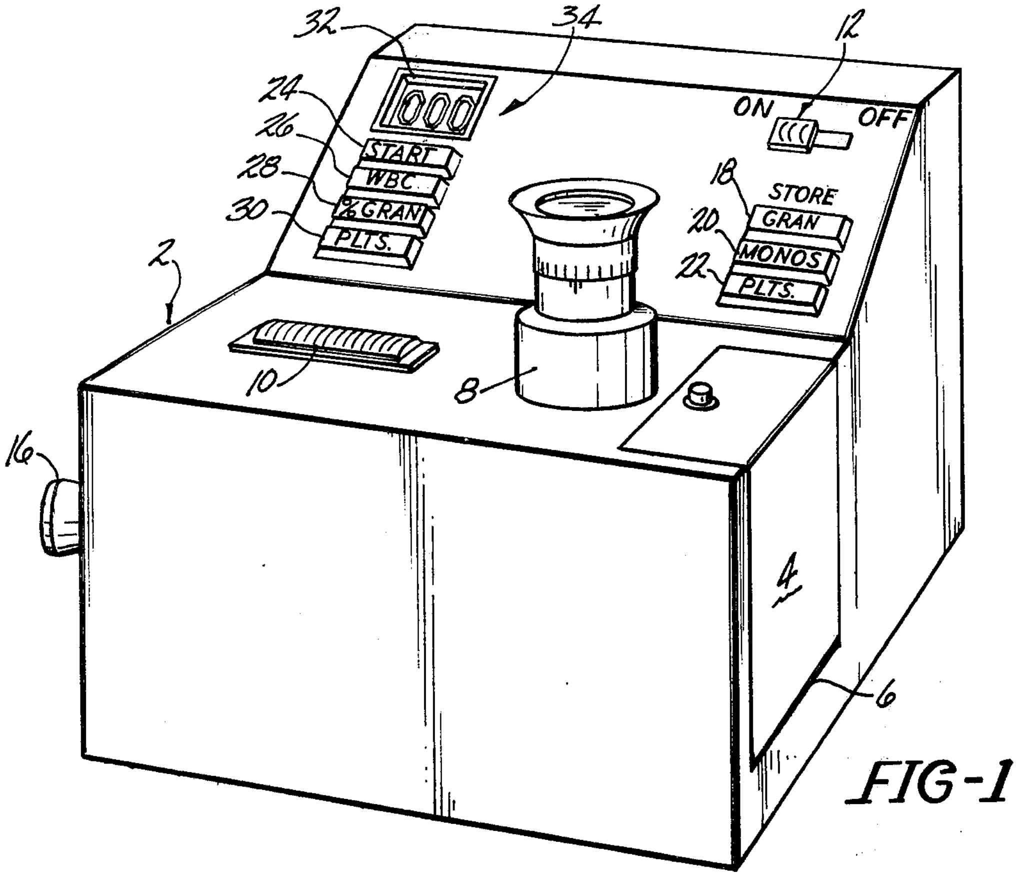
FIG. 1 is a perspective view of a preferred embodiment of an instrument for measuring the distance between the menisci of a layer of cells in a centrifuged blood sample in accordance with this invention.
Figure 2:
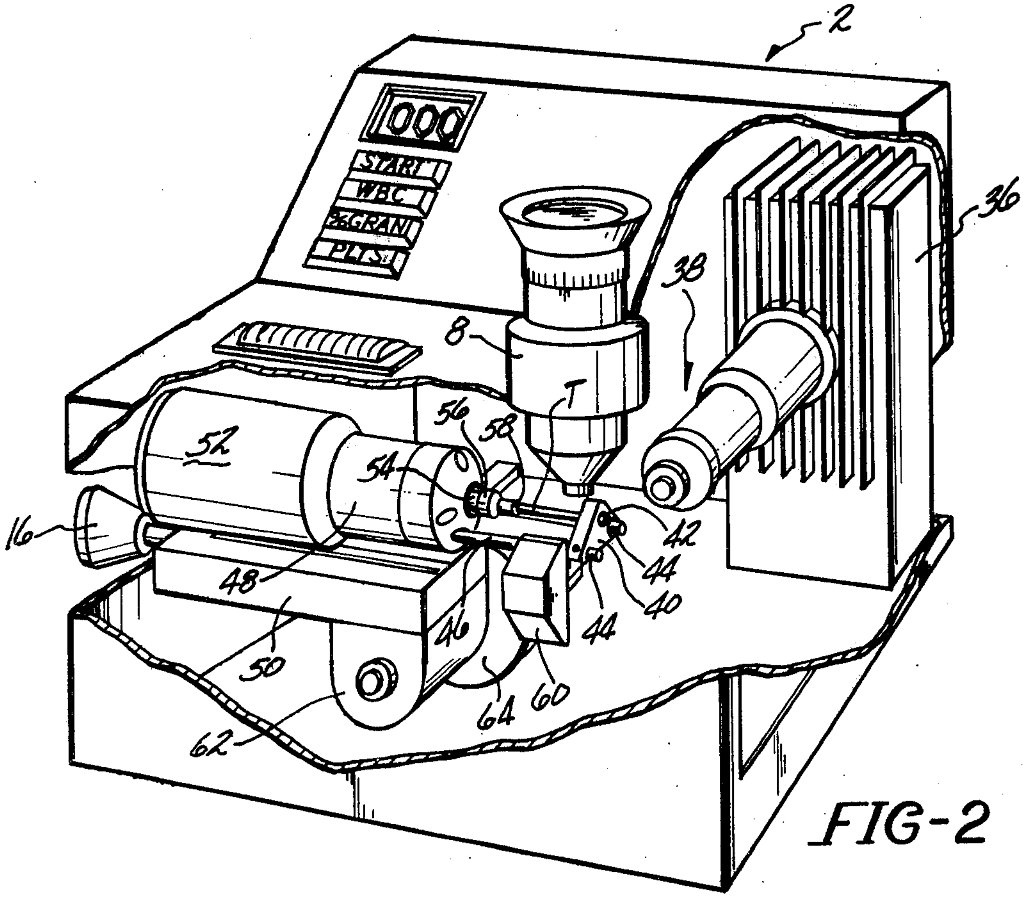
FIG. 2 is a perspective view similar to FIG. 1 but showing the instrument case broken away to disclose the internal components of the instrument.

Referring now to the drawings, there is shown in FIGS. 1 and 2 a preferred embodiment of a blood testing instrument which operates in accordance with this invention. The instrument includes a casing 2 in which the operative elements of the instrument are housed. The casing 2 includes a door 4 mounted thereon by means of a piano hinge 6. The door 4 is opened to permit mounting of the capillary tube to be tested in place, and then closed to prevent ambient light from entering the inside of the casing. A lens housing 8 is mounted on the casing and contains the optics preferred for use in properly aligning the menisci of a cell layer during measurement of the thickness of the cell layer. A simple calibrated scale 10 is disposed on the casing 2 for making a general measurement of the red cell layer thickness in the centrifuged blood sample in the capillary tube prior to inserting the latter into the instrument. The scale 10 is pre-calibrated to provide an approximate hematocrit count based on the observed thickness of the centrifuged red cell layer in the capillary tube. An on-off switch 12 is disposed on the casing for turning the instrument on and off. A stage-advancing dial 16 protrudes from the casing for advancing the specimen-holding stage within the casing 2, as will also be explained in greater detail hereinafter. Three data-storing electrical switch buttons 18, 20 and 22 protrude from the casing 2 for use in a manner which will be explained in greater detail hereinafter. An electrical start button 24 is positioned on the casing and operates in a manner described hereinafter with greater detail. Three data-readout electrical switch buttons 26, 28 and 30 are disposed on the casing and operate in a manner which will be described hereinafter in greater detail. The casing 2 also includes a window 32 through which a digital readout device 34 can be seen.

Referring now to FIG. 2, there is shown the components of the instrument which are disposed inside of the case 2. A light source 36 is disposed in the casing 2 and a focussing lens system is disposed in a housing 38. The capillary tube T which contains the blood sample to be tested is mounted in the support assembly within the casing 2. The support assembly includes one end plate portion 40 in the shape of a triangle. At the upper apex of the triangle, there is formed a through passage 42 in which one end of the tube T is journalled for rotational movement. The lower apices of the plate 40 are formed with through passages 44 which receive rods 46 serving to connect the plate 40 to a block 48 which is mounted on a stage 50. Adjacent to the block 48 and also mounted on the stage 50 is an electric motor 52, the shaft of which extends through a central axial passage in the block 48. Attached to the end of the motor shaft 54 is a collar 56 made of elastomeric material. The collar 56 includes a recess 58 which forms a chuck for receiving the other end of the tube T. A prism 60 is mounted in the casing 2 and positioned so as to direct the light from the source 36 toward the tube T from the direction which will produce optimum fluorescence of the stain in the blood sample toward the lenses in the measuring lens housing 8. A gear box 62 is disposed below the stage 50 and a potentiometer 64 is disposed adjacent to the gear box 62. The stage-advancing dial 16 is operably connected to the gears in the gearbox 62 and to the potentiometer in a manner set forth in greater detail hereinafter. The dial 16 is also operably connected to the stage 50 so as to be capable of reciprocably moving the stage 50.

Figure 3:
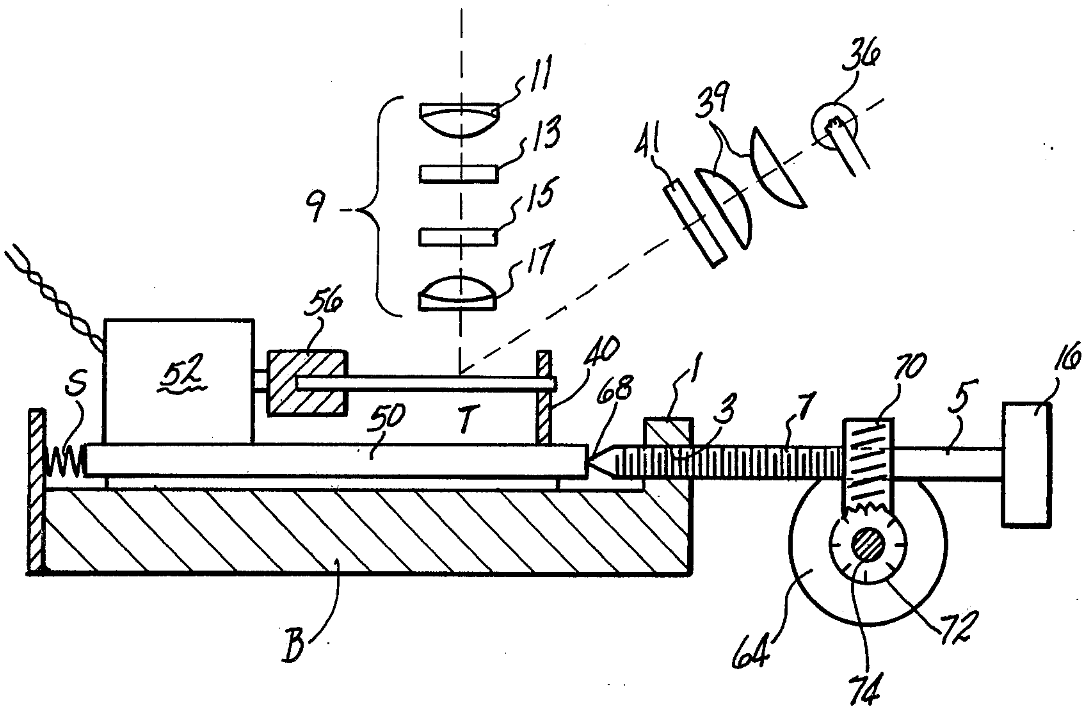
FIG. 3 is a somewhat schematic representation of the details of the operable parts of the instrument of FIG. 1.

Referring now to FIG. 3, there is shown a somewhat schematic representation of a working embodiment of an apparatus which operates in accordance with the invention. As previously noted, the spinner motor 52 is mounted on the stage 50 which, in turn, is reciprocably mounted on a base portion B. Also mounted on the stage 50 is the passive portion of the tube support, the plate 40. The chuck 56 holds the other end of the tube T and is rotatably driven by the motor 52. The fixed base B, which is part of the instrument casing, is formed with an upstanding flange 1 through which extends a threaded hole 3. The dial 16 has secured thereto an actuating rod 5 which has an inner threaded end portion 7 which is screwed into and through the threaded hole 3. The inner end 68 of the rod 5 bears against one end of the stage 50, with the stage 50 being biased theretoward by a spring S. Mounted on the shaft 5 is a first gear 70 which is keyed to the shaft 5 to rotate therewith. A second gear 72 meshes with the first gear and rotates therewith at a 1:3 ratio. The second gear 72 is keyed to a shaft 74 which forms the drive of a potentiometer 64. Thus rotation of the potentiometer drive 74 is proportional to the linear movement of the stage 50. The light source 36 is focussed by condensing lenses 39 which are mounted in the housing 38. A filter 41 is mounted in the housing 38 which allows transmission of the desired excitation light wavelengths of light to provide maximum excitation of the stain but blocks other wavelengths. The optical viewing assembly which is mounted in the housing 8 consists of an assembly 9 comprising an ocular lens assembly 11, hair-line reference line 13, light filter 15, and an objective lens assembly 17. The range of magnification of the lens system in the assembly 9 is preferably from 4 to 20x. The hair-line reticle 13 is preferably positioned at the focal plane of the ocular lens set 11 so that the assembly 9 is parallax-free. The filter 15 removes the wavelengths of the illuminating excitation light and transmits only the fluorescent wavelengths of light emitted by the fluorescing stained cells in the capillary tube T.

Figure 4:
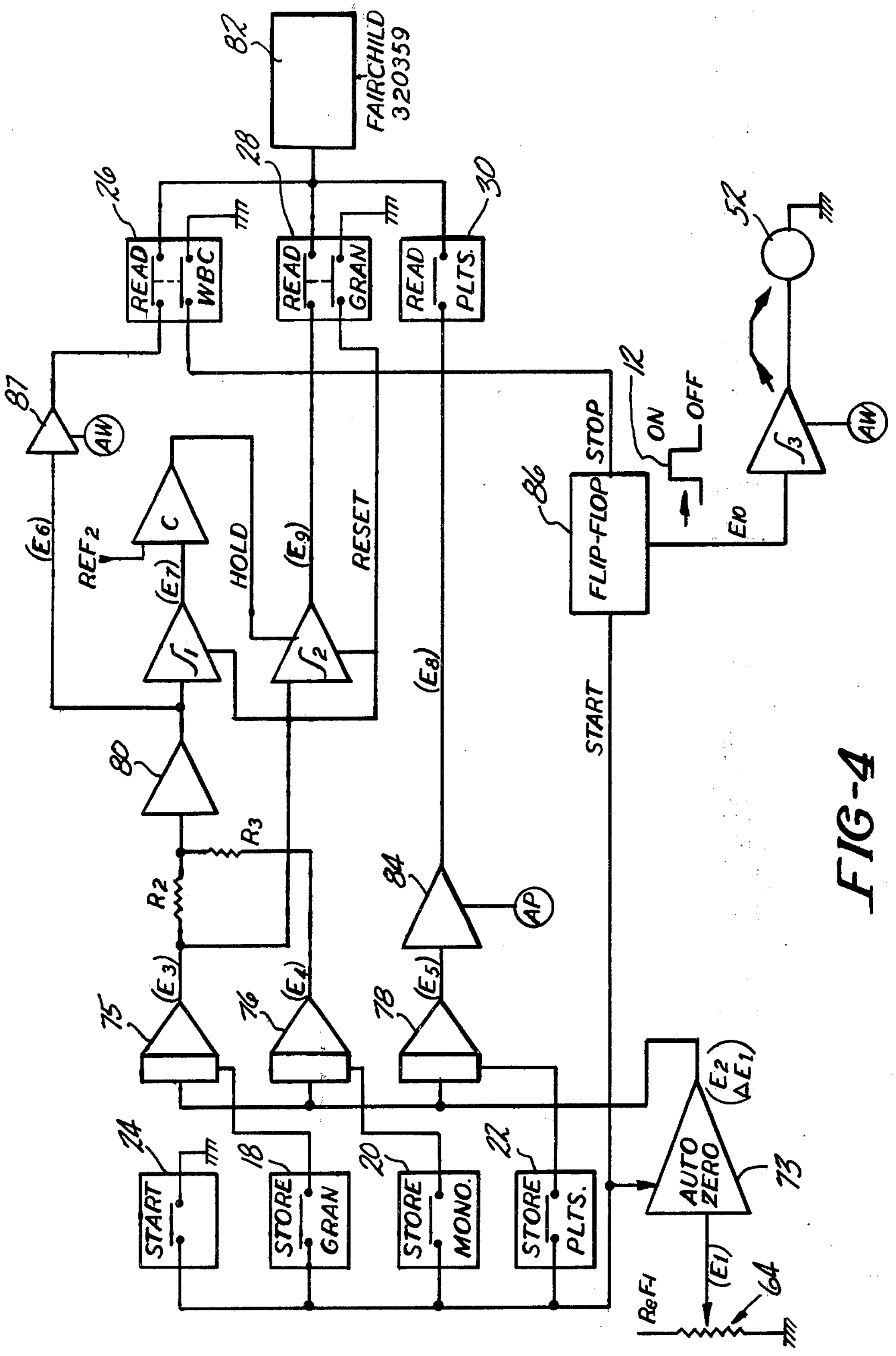
FIG. 4 is a diagrammatic representation of a portion of the electrical circuitry preferred for use in the instrument shown in FIG. 1.

Referring now to FIG. 4, the mode of operation of the instrument will be explained, along with the electronics. After the "on-off" switch is turned to "on", and to begin the reading process, the capillary tube T is placed in the chuck and the stage 50 is manually adjusted by means of the dial 16 to align the reference line with the red cell/granulocyte interface. The start button (switch) 24 is depressed which starts the motor 52 and causes activation of an "auto zero" amplifier 73. The input voltage to the amplifier 73 is derived from a voltage divider potentiometer 64 which produces a voltage proportional to the position of the stage 50, as previously described. Actuation of the "auto zero" amplifier 73 automatically nulls out any existing input voltage $E_1$. Subsequent changes in the input voltage $E_1$ appear at the output $E_2$ of the amplifier 73. This output voltage $E_2$ is presented to the inputs of each of the sample and store amplifiers 75, 76 and 78.

The stage 50 is then advanced with the dial 16 until the reference line 13 is exactly aligned with the interface between the granulocyte and mononuclear cell layers. The output voltage $E_2$ of the amplifier 73, at this point, represents a value which is proportional to the number of granulocytes, i.e., the axial dimension of that cell layer. The "store gran." button (switch) 18 is then depressed and the voltage $E_2$ is stored in the amplifier 75. Further movement of the potentiometer 64 causes no change in the output of the amplifier 75. The "auto zero" amplifier 73 is also actuated by depressing the "store gran." switch 18 thus resetting the output $E_2$ of the "auto zero" amplifier 73 to zero.

The stage 50 is then advanced to align the reference line 13 with the interface between the mononuclear cell layer and the platelet layer. The "store monos" switch 20 is then depressed which results in storage of the new output $E_2$ in the amplifier 76 and resets the "auto zero" amplifier 73 output $E_2$ to zero.

The stage 50 is then again advanced to align the reference line 13 with the interface between the platelet cell layer and the plasma layer. The "store plts" switch 22 is then depressed to store the new output $E_2$ in the amplifier 78 and the output $E_2$ of the "auto zero" amplifier 73 is then returned to zero. All of the readings have then been taken and stored and are ready to be read.

To read the results, the "read" switches 26, 28 and 30 may be depressed in any order. The white blood count (WBC) is the sum of the granulocyte layer and the mononuclear layer. The output voltages $E_3$ and $E_4$ of the amplifiers 75 and 76 respectively are summed in a summing amplifier 80. Resistors $R_2$ and $R_3$ are chosen to reflect the particular packing coefficients of the granulocytes and mononuclears. This permits the digital panel to display a cell count number for each cell layer measured despite the fact that the different cell types are of different size and pack differently. For example, there could be 500 granulocyte cells per 0.001" measurement but 1000 mononuclear cells packed into an 0,001" layer. The scaling is adjusted by amplifier 87 and potentiometer Aw to provide an output calibrated to cells/cubic millimeter. Depressing the "read WBC" switch 26 transfers the output voltage of the scaling amplifier 87 to the digital panel meter 82, which is preferably a Fairchild 320359 meter. Depressing the switch 26 also stops rotation of the motor 52.

Depressing the "read % gran" switch 28 switches the digital panel meter 82 to read the output voltage $E_9$ and simultaneously resets integrators $S_1$ and $S_2$. Integrators $S_1$ is driven from output voltage $E_6$ which represents the total white blood count. Integrator $S_2$ is driven from output voltage $E_3$, which represents the granulocyte count. The output of integrator $S_1$ goes to a comparator C. When the output voltage $E_7$ of the integrator $S_1$ reaches the voltage of Ref 2, the output voltage of $S_2$ will be held at whatever voltage is present at that time. Ref 2 is chosen so that $E_9$ would produce a reading of 100 on the digital panel meter 82 if all of the cells were granulocytes, i.e., if $E_4$ were equal to zero. Thus $E_9$ will be the ratio of $E_3/(E_3+E_4)\times 100$.

Depressing the "read plts" switch 30 connects the output voltage $E_8$ to the digital panel meter. The stored platelet voltage $E_5$ is scaled by an amplifier 84 to produce a voltage $E_8$ which will produce a reading of platelets per cubic millimeter times 1000. The appropriate scale factor is provided by potentiometer Ap.

The "flip-flop" switch 86 is a bi-stable switch controlled by the switches previously described. When turned on, its output $E_{10}$ changes state from low to high. This output drives an integrator $S_3$. The output of $S_3$ powers the spinner motor 52. The slow ramp-up and ramp-down of the integrator $S_3$ causes the motor 52 to start and stop at a slow, controlled rate, thus preventing the cell layers from being disturbed. Adjustment Aw controls the maximum output voltage of $S_3$, thus acting as a maximum motor speed control.

It will be readily appreciated that the instrument of the invention will provide accurate cell counts which are accurately displayed for recordal. In place of the electrical system preferred for providing the numerical cell count readouts, a simpler mechanical system could be utilized if desired. Regarding the details of the disclosed embodiment of the electrical storage and readout system, other means for sensing movement of the stage, converting the sensed movement into an electrical signal, and converting the signal into intelligible indicia could be used without departing from the scope of the invention.

Since many changes and variations of the disclosed embodiment of the invention may be made without departing from the inventive concept, it is not intended to limit the invention otherwise than as required by the appended claims.

What is claimed is:

1. An instrument for use in measuring approximate cell counts of predetermined constituent blood cell layers which are differentially colored with a fluorescent stain and which are in a centrifuged anticoagulated blood sample contained in a transparent capillary tube, said instrument comprising:

(a) first means for holding the capillary tube;

(b) an optically magnifying parallax-free, ocular type optical system mounted for focussing on the cell layers, said optical system including means forming a reference line extending transversely of the axis of the capillary tube;

(c) light source means mounted to be directed at the capillary tube to highlight the differential coloring of the blood cell layers being measured;

(d) means for causing relative movement between said reference line and the capillary tube to occur in a direction longitudinal of the capillary tube;

(e) indicating means for providing a visible numerical indicia which is proportional to the extent of movement between said reference line and the capillary tube from commencement of the movement to termination thereof;

(f) first filter means operable to filter out all but a first predetermined narrow wavelength band of light directed at the capillary tube from said light source means, and second filter means operable to filter out all but a second predetermined narrow wavelength band of light eminating from the fluorescently colored blood cell layers and directed toward said optical system; and (g) means connected to said first means for spinning the capillary tube about its axis at a rate operable to optically average miniscus uneveness.

2. The instrument of claim 1, wherein said indicating means includes electrical means for providing a digital readout and for automatically sensing the extent of movement between said reference line and the capillary tube and converting sensed and observed increments of movement into indicia at said digital readout which substantially correspond to a cell concentration for a cell layer being measured.

3. An instrument for use in measuring approximate cell counts of predetermined constituent blood cell layers which are differentially colored with a fluorescent stain and which are contained in a centrifuged anticoagulated blood sample disposed in a transparent capillary tube, said instrument comprising:

(a) mounting means for engaging and supporting at least one end portion of the capillary tube;

(b) an optically magnifying, parallax-free, ocular type optical system mounted for focussing on the cell layers in the supported capillary tube, said optical system including a reference line for alignment with interfaces between adjacent cell layers;

(c) a light source mounted to direct a beam of light along a path toward the capillary tube to cause the stain in the blood sample to fluoresce;

(d) first filter means disposed between said light source and the capillary tube for filtering out substantially all wavelengths of light except the wavelength of light which most actively energizes the fluorescent stain to cause maximum fluorescence of the stain to occur;

(e) second filter means disposed between at least a part of said optical system and the capillary tube for filtering out at least the fluorescent stain-energizing wavelengths of light while transmitting the fluorescent light wavelengths emitted by the fluorescent stain;

(f) actuating means operably connected to the capillary tube for moving the latter in a direction corresponding to the direction of the longitudinal axis of the capillary tube;

(g) readout means for providing a visible numerical indication of the cell count in a predetermined cell layer, said indication being proportional to the extent of movement of the capillary tube from a first position corresponding to a first cell interface to a second position corresponding to a second cell interface; and (h) means connected to said mounting means for spinning the capillary tube about its axis of elongation at a rate operable to optically average miniscus uneveness.

4. The instrument of claim 3, wherein said readout means includes a digital readout panel operated by electrical means for automatically sensing the extent of movement imparted to the capillary tube and producing numerical indicia at said readout panel, which indicia correspond to cell concentrations for a cell layer being measured.

5. An instrument for use in measuring approximate cell counts of predetermined constituent blood cell layers which are differentially colored with a fluorescent stain and which blood cell layers are contained in a centrifuged anticoagulated blood sample disposed in a transparent capillary tube, said instrument comprising:

(a) mounting means for engaging and supporting the capillary tube so as not to obstruct viewing of the predetermined constituent blood cell layers;

(b) an optically magnifying, parallax-free, ocular-type optical system mounted for focussing on the cell layers in the supported capillary tube, said optical system including a reference line for alignment with interfaces between adjacent cell layers;

(c) a light source positioned so as to direct a beam of light along a path toward the capillary tube to cause the stain in the blood sample to fluoresce;

(d) means for moving the capillary tube in the direction of its axial elongation;

(e) electrical means including a readout portion, said electrical means being operable to automatically sense the extent of movement imparted to the capillary tube and produce numerical indicia at said readout portion which indicia correspond to a cell concentration for a cell layer being measured, said electrical means further comprising means for compensating for different cell sizes and cell packing characteristics found in the different cell layers being measured whereby the same increments of length measured in different cell layers will result in different numerical indicia being produced at said readout portion;

(f) first filter means disposed between said light source and the capillary tube for permitting passage of substantially only the wavelengths of light from the light source which provide maximum excitation for the fluorescent stain; and (g) second filter means disposed between the capillary tube and the eye of a viewer looking through said optical system for permitting passage of substantially only the wavelengths of light caused by fluorescence of the fluorescent stain.

6. The instrument of claim 5, wherein said readout portion is a digital display panel.

7. The instrument of claim 5, further comprising means connected to said mounting means for spinning the capillary tube about its axis of elongation at a rate operable to optically average miniscus uneveness.

8. An instrument for use in measuring approximate cell counts of predetermined constituent blood cell layers which are differentially colored with a fluorescent stain and which blood cell layers are contained in a centrifuged anticoagulated blood sample disposed in a transparent capillary tube, said instrument comprising:

(a) mounting means for engaging and supporting the capillary tube so as not to obstruct viewing of the predetermined constituent blood cell layers;

(b) an optical system mounted for focussing on the cell layers in the supported capillary tube, said optical system including a reference line for alignment with interfaces between adjacent cell layers;

(c) a light source positioned so as to direct a beam of light along a path toward the capillary tube to cause the stain in the blood sample to fluoresce;

(d) means for moving the capillary tube in the direction of its axial elongation;

(e) monitoring means for sensing the extent of movement of the tube and translating the extent of movement into a visible indication of cell concentration proportional to the extent of movement; and (f) means for spinning the capillary tube about its axis of elongation during measurement to cause apparent optical averaging of the cell interfaces so that the latter appear to be even.

9. The instrument of claim 8, further comprising first filter means disposed between said light source and the capillary tube and operable to filter out from said beam of light substantially all but a predetermined wavelength band of light, the latter of which provides maximum excitation of the fluorescent stain; and second filter means operably associated with said optical system to filter out substantially all wavelengths of light eminating from the capillary tube except for the wavelengths of light produced by excitation of the fluorescent stain.

10. The instrument of claim 8, wherein said monitoring means includes electrical means for providing a digital readout and for automatically sensing the extent of movement of the capillary tube and converting sensed and observed increments of movement into indicia at said digital readout which substantially correspond to a cell concentration for a cell layer being measured.

11. The instrument of claim 10, wherein said electrical means includes means for properly adjusting said numerical indicia to compensate for different cell sizes and cell packing characteristics found in different cell layers being measured whereby the same increments of length measured in different cell layers will result in different numerical indicia being produced at said digital readout.

12. A method for measuring the approximate cell count in a constituent cell layer in a centrifuged sample of anticoagulated blood contained in a capillary tube, said method comprising the steps of:

(a) staining the cell layer to be measured a color which is distinctively different from adjacent cell layers;

(b) directing a beam of light at the cell layer to be measured to illuminate the latter;

(c) spinning the capillary tube about its axis of elongation at a rate operable to optically average miniscus uneveness;

(d) measuring the distance between opposite interfaces of the cell layer to be measured; and (e) converting the measured distance to a numerical indication of the concentration of cells in the cell layer being measured.

13. An instrument for use in measuring approximate cell counts of predetermined constituent blood cell layers which are in a centrifuged anticoagulated blood sample contained in a transparent capillary tube, said instrument comprising:

(a) first means for holding the capillary tube;

(b) detecting means for detecting the presence of the different blood cell types when the different blood cell types pass through a predetermined plane within the instrument;

(c) light source means mounted to be directed at the capillary tube to render the different cell types distinguishable to said detecting means;

(d) means for causing relative movement between said predetermined plane and the capillary tube to occur in a direction longitudinal of the capillary tube; and (e) electrical means including a readout portion, said electrical means being operable to automatically sense the extent of movement imparted to the capillary tube and produce numerical indicia at said readout portion which indicia correspond to a cell concentration for a cell layer being measured, said electrical means further including means for compensating for different cell sizes and cell packing characteristics found in the different cell layers being measured whereby the same increments of length measured in different cell layers will result in different numerical indicia being produced at said readout portion.

14. The instrument of claim 13, further comprising means for spinning the capillary tube about its axis at a rate operable to produce optical averaging of miniscus uneveness at cell layer interfaces.

* * * * *